(12) United States Patent
Steed (10) Patent No.: US 10,967,669 B2
(45) Date of Patent: Apr. 6, 2021

(54) SCENTED FLOWER PEN ARRANGEMENT

(71) Applicant: Amanda Steed, Fort Collins, CO (US)

(72) Inventor: Amanda Steed, Fort Collins, CO (US)

(73) Assignee: Amanda Steed, Fort Collins, CO (US)

( * ) Notice: Subject to any disclaimer, the term of this patent is extended or adjusted under 35 U.S.C. 154(b) by 297 days.

(21) Appl. No.: 16/270,577

(22) Filed: Feb. 7, 2019

(65) Prior Publication Data

US 2019/0241007 A1   Aug. 8, 2019

Related U.S. Application Data (60) Provisional application No. 62/627,592, filed on Feb. 7, 2018.

(51) Int. Cl.
*B43K 29/00* (2006.01)
*A47G 7/06* (2006.01)
*A41G 1/00* (2006.01)

(52) U.S. Cl.
CPC .............. *B43K 29/00* (2013.01); *A41G 1/001* (2013.01); *A47G 7/06* (2013.01)

(58) Field of Classification Search
CPC .......... A47G 7/06; A41G 1/001; A41G 1/006; B43K 29/00; B43K 31/00; B43K 23/002; B43M 99/006
USPC .................................................. 401/195, 131
See application file for complete search history.

(56) References Cited

U.S. PATENT DOCUMENTS

| | | | | |
|---|---|---|---|---|
| 2,929,511 | A * | 3/1960 | Josephson | B21F 45/00 211/60.1 |
| 6,773,188 | B1 * | 8/2004 | Tamaye | B43K 7/005 401/131 |
| 9,004,377 | B1 * | 4/2015 | Whittaker | A47G 7/06 239/34 |
| 9,844,974 | B2 * | 12/2017 | McCurdy | A41G 1/00 |
| 2008/0066379 | A1 * | 3/2008 | Carter | A01G 9/024 47/67 |
| 2015/0151564 | A1 * | 6/2015 | Jones | B42K 7/005 401/208 |
| 2019/0054759 | A1 * | 2/2019 | Chen | B43M 99/006 |

FOREIGN PATENT DOCUMENTS

| | | | | |
|---|---|---|---|---|
| DE | 202007008302 U1 * | 11/2007 | | A47G 7/06 |
| DE | 202008000883 U1 * | 6/2009 | | A47G 7/06 |

\* cited by examiner

*Primary Examiner* — Erin Deery
(74) *Attorney, Agent, or Firm* — Amanda Steed (57) ABSTRACT

A scented flower writing utensil arrangement has a vase, an artificial floral arrangement, a quantity of simulated water medium, a scented core, a writing utensil holder, and a plurality of decorative writing utensils. The quantity of simulated water medium is a self-curing agent at the base of the vase within which the stems of the artificial floral arrangement are affixed. The scented core and the writing utensil holder are disguised within the artificial floral arrangement. The scented core is a sponge or similar material to which scented oil is applied. Each of the plurality of decorative writing utensils has a flower end opposite the writing end, and is placed into the writing utensil holder.

9 Claims, 11 Drawing Sheets

SCENTED FLOWER PEN ARRANGEMENT

The current application claims a priority to the U.S. Provisional Patent application Ser. No. 62/627,592 filed on Feb. 7, 2018.

FIELD OF THE INVENTION

The present invention relates to artificial flower arrangements. More particularly, the present invention relates to a scented artificial flower arrangement that holds writing utensils.

BACKGROUND OF THE INVENTION

In present times, individuals are always trying to find ways to decorate their offices. Individuals often decorate their offices with floral arrangements that comprises of live plants, but their work-desk may be unsuitable for live floral plants. Instead, individuals would often opt for artificial floral arrangements on their office desks, but they only serve as aesthetic pieces which may potentially contribute to work-desk clutter. The present invention introduces a practical artificial floral arrangement. The present invention simulates a fresh bouquet of flowers and comprises of useful features that not only makes it aesthetically pleasing, but practical as well. The present invention also acts as an air-freshener, where the present invention will be pre-infused with natural scents. The present invention is primarily used for office usage but can also be useful in any household countertop. The present invention is intended to be a creative, yet useful gift that any user can enjoy.

Additional advantages of the invention will be set forth in part in the description which follows, and in part will be obvious from the description, or may be learned by practice of the invention. Additional advantages of the invention may be realized and attained by means of the instrumentalities and combinations particularly pointed out in the detailed description of the invention section. Further benefits and advantages of the embodiments of the invention will become apparent from consideration of the following detailed description given with reference to the accompanying drawings, which specify and show preferred embodiments of the present invention.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

The present invention is a scented flower arrangement for decoration and holding writing utensils. In general, the present invention comprises a vase 1, an artificial floral arrangement 2, a quantity of simulated water medium 3, a scented core 4, a writing utensil holder 5, and a plurality of decorative writing utensils 6.

Referring to FIGS. 1-7, the vase 1 is a vessel for holding and supporting the rest of the components of the present invention. In various embodiments, the vase 1 may comprise many different shapes and sizes, so long as the vase 1 is capable of containing and supporting the various components of the present invention. The vase 1 may be made of any desirable material, such as, but not limited to: glass, ceramic, or metal, may be translucent or opaque, and may comprise any desirable decorations or visual embellishments on its exterior. In various embodiment of the present invention, the vase 1 can be any type of container of varying shapes, sizes, translucency, and/or color that can secure and stabilize the artificial floral arrangement 2. The vase 1 generally comprises a base 11, a brim 12, and an opening 13. The base 11 is the end of the vase 1 that rests atop a surface that the present invention is to rest upon. More specifically, the base 11 serves as the foundation to the vase 1, where it provides stability to the configuration of the present invention. The base 11 and the brim 12 are positioned opposite each other along the vase 1 and are connected by one or more lateral walls. More specifically, the brim 12 is the open top end of the vase 1 that the artificial floral arrangement 2 rests on. In embodiments where the vase 1 is cylindrical in shape, the brim 12 and the vase 1 are connected to each other by a single wall with a circular cross-section. In embodiments where the vase 1 may have a rectangular cross-section, for example, the brim 12 and the vase 1 are connected to each other by four lateral walls. The opening 13 is delineated by the brim 12, and any objects placed into the vase 1 must pass through the opening 13.

The quantity of simulated water medium 3, as illustrated by FIGS. 7-10, is positioned within the vase 1 adjacent to the brim 12. In the preferred embodiment, the quantity of simulated water medium 3 is a self-curing agent which may be poured into the vase 1 and cures over time into a hardened, clear form in order to simulate the presence of water while precluding the need to be mindful of the presence of any water when handling the present invention. Various components of the present invention may be positioned into the quantity of simulated water medium 3 simultaneously as the self-curing agent is placed into the vase 1, so as to permanently affix said components within the quantity of simulated water medium 3 after the curing process. The quantity of simulated water medium 3 permanently secures and anchors the artificial floral arrangement 2 in place within the vase 1. Additionally, the glass serves as a counterweight to prevent the bed assembly from becoming top heavy. The composition of the quantity of simulated water medium 3 may vary, and various different self-curing agents or other materials may be utilized so long as the aforementioned purposes are fulfilled.

The artificial floral arrangement 2 is a bouquet of artificial flowers, providing an aesthetically pleasing appearance to the user. The artificial floral arrangement 2 may comprise any desired quantity and variety of artificial flowers and/or other artificial plants. The artificial floral arrangement 2 traverses into the vase 1 through the opening 13 and comprises a plurality of flowers and a plurality of stems, with each of the plurality of flowers being terminally connected to one of the plurality of stems. The plurality of flowers can vary in shapes, arrangements, colors, and/or sizes in various embodiments of the present invention. The artificial floral arrangement 2 may further comprise a plurality of petals or leaves in addition to the plurality of flowers. The plurality of stems is connected within the quantity of simulated water medium 3; more particularly, the plurality of stems is inserted into the quantity of simulated water medium 3 before curing in order to permanently affix the artificial floral arrangement 2 within the vase 1. The plurality of flowers is positioned above the brim 12 of the vase 1 while installed into the quantity of simulated water medium 3 in order to provide an aesthetically pleasing appearance.

Figure 4:
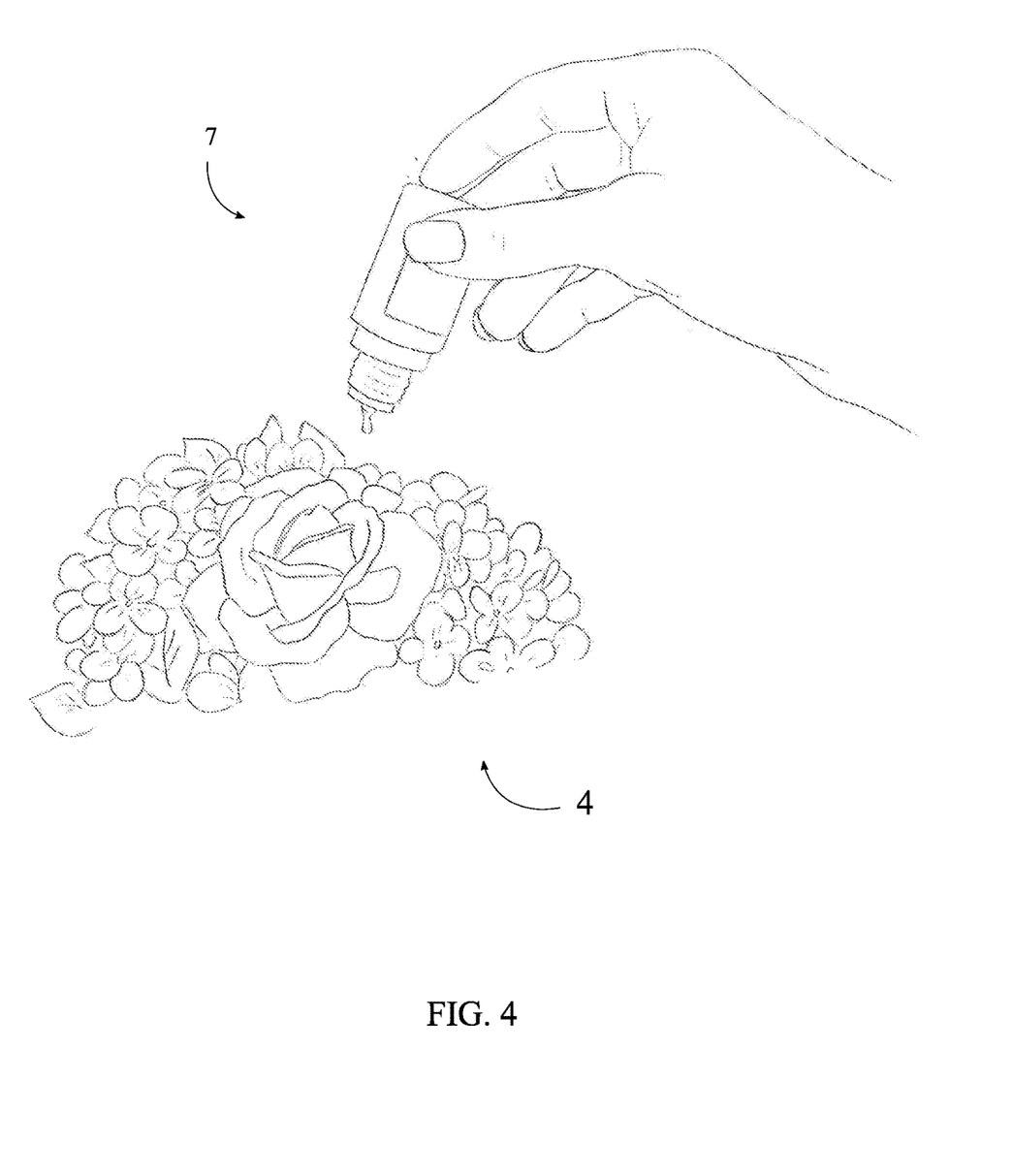
FIG. 4 is a perspective view of a flower used in the present invention that shows a quantity of scented oil applied onto an exemplary scented core in one embodiment of the present invention.

In the preferred embodiment of the present invention, the scented core 4 is a sponge, though in various embodiments, the scented core 4 may be any other type of object suitable for facilitating dispersal of scented oil or other forms of scent dispersal medium. More specifically, the sponge is an absorbent foamy material that retains and disperses the oil across the artificial flower 61 arrangement. To this end, the present invention further comprises a quantity of scented oil 7 distributed onto the scented core 4. Since the scented oil may evaporate over time, the user may be required to resupply the scented core 4 with further quantities of scented oil or other scented media. More specifically, the oil is a floral essential oil that provides the bouquet with a realistic smell. In the various embodiments of the present invention, the oil can be any scent that the user desires. It is contemplated that the scented core 4 may be placed in any desirable location within the artificial flower 61 arrangement. In some embodiments, the scented core 4 forms a stabilizing base 11 for the artificial flower 61 arrangement, with the stems of the artificial flower 61 arrangement puncturing through the scented core 4 such that the scented core 4 rests approximately in the middle of the flowers and stems.

Figure 9:
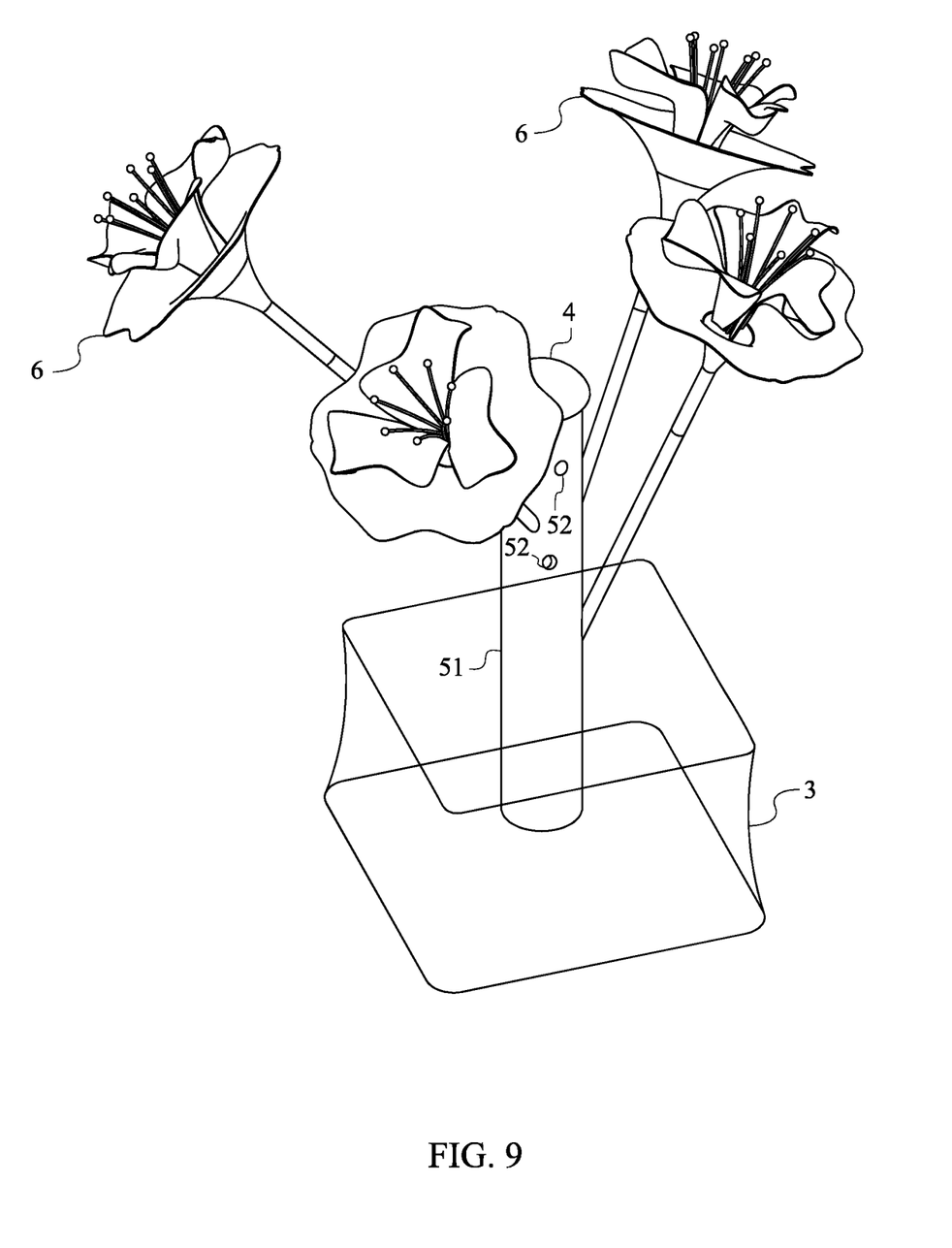
FIG. 9 is a perspective view of one embodiment of the present invention with the vase and artificial floral arrangement not shown.
Figure 10:
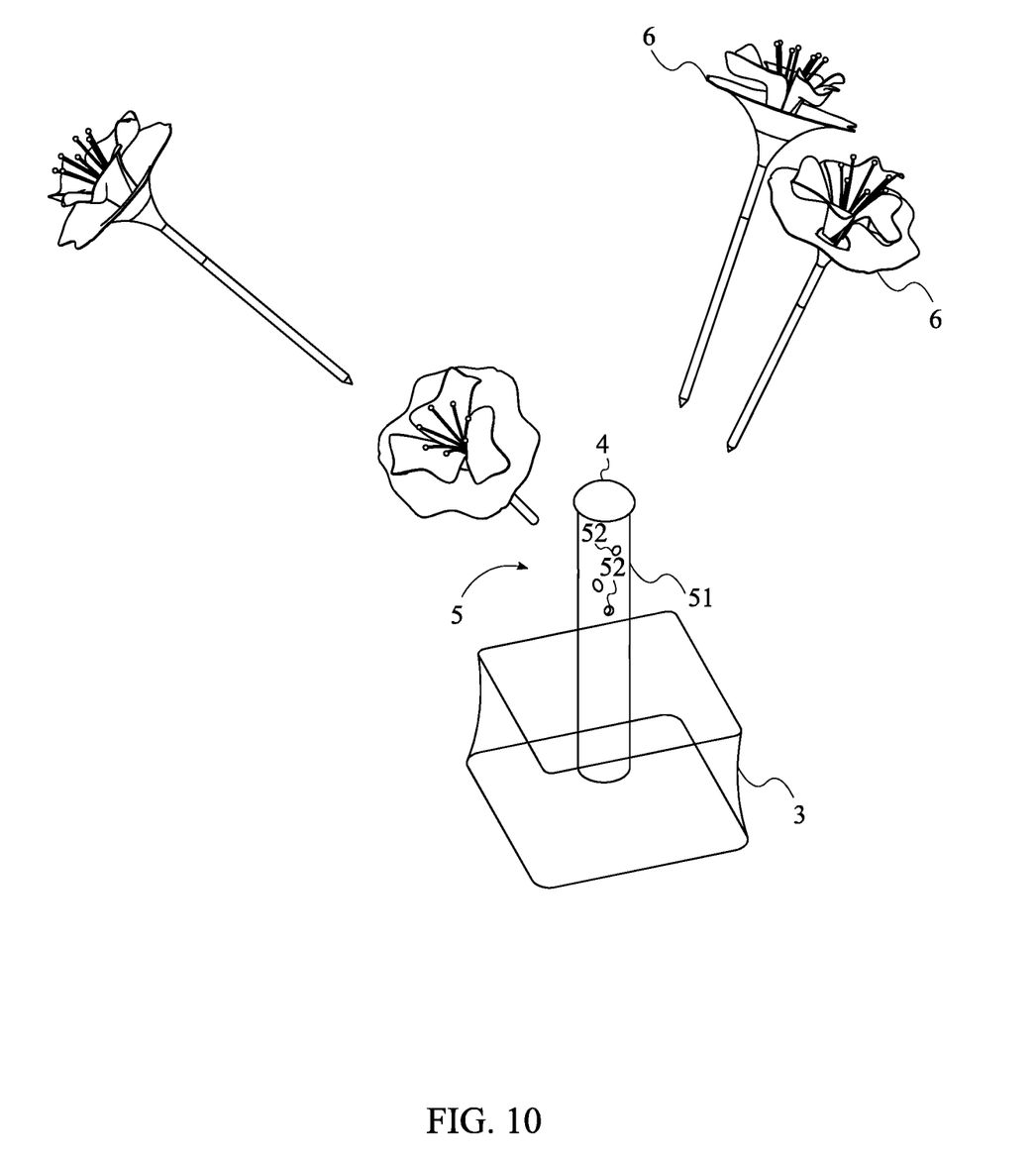
FIG. 10 is an exploded perspective view of one embodiment of the present invention with the vase and artificial floral arrangement not shown.

Referring to FIGS. 9-10, the writing utensil holder 5 comprises a body 51 and a plurality of receptacles 52, with each of the plurality of receptacles 52 traversing into the body 51 of the writing utensil holder 5. Each of the plurality of decorative writing utensils 6 is removably positioned into one of the plurality of receptacles 52 of the writing utensil holder 5. Furthermore, the writing utensil holder 5 may be affixed into the quantity of simulated water medium 3 in some embodiments. In some embodiments, each of the plurality of receptacles 52 comprises a flared lip, forming a funnel shape as the entrance to each of the receptacles 52 in order to facilitate easy placement of writing utensils into the receptacles 52. Furthermore, in some embodiments, the flared lip may resemble the sepal portions of a rose, as if the petals, stigma, style, and ovary of the rose had been removed in order to facilitate the writing utensil holder 5 being camouflage into the artificial floral arrangement 2.

The artificial floral arrangement 2 is arranged around the scented core 4 and the writing utensil holder 5. Preferably, the stems of the artificial floral arrangement 2 are either glued with adhesive onto the sides of the writing utensil holder 5, or are affixed within the quantity of simulated water medium 3 adjacent to the body 51 of the writing utensil holder 5 in order to camouflage the writing utensil holder 5 into the artificial floral arrangement 2. Furthermore, the writing utensil holder 5 is preferably colored green to match the stems of the artificial floral arrangement 2.

Figure 1:
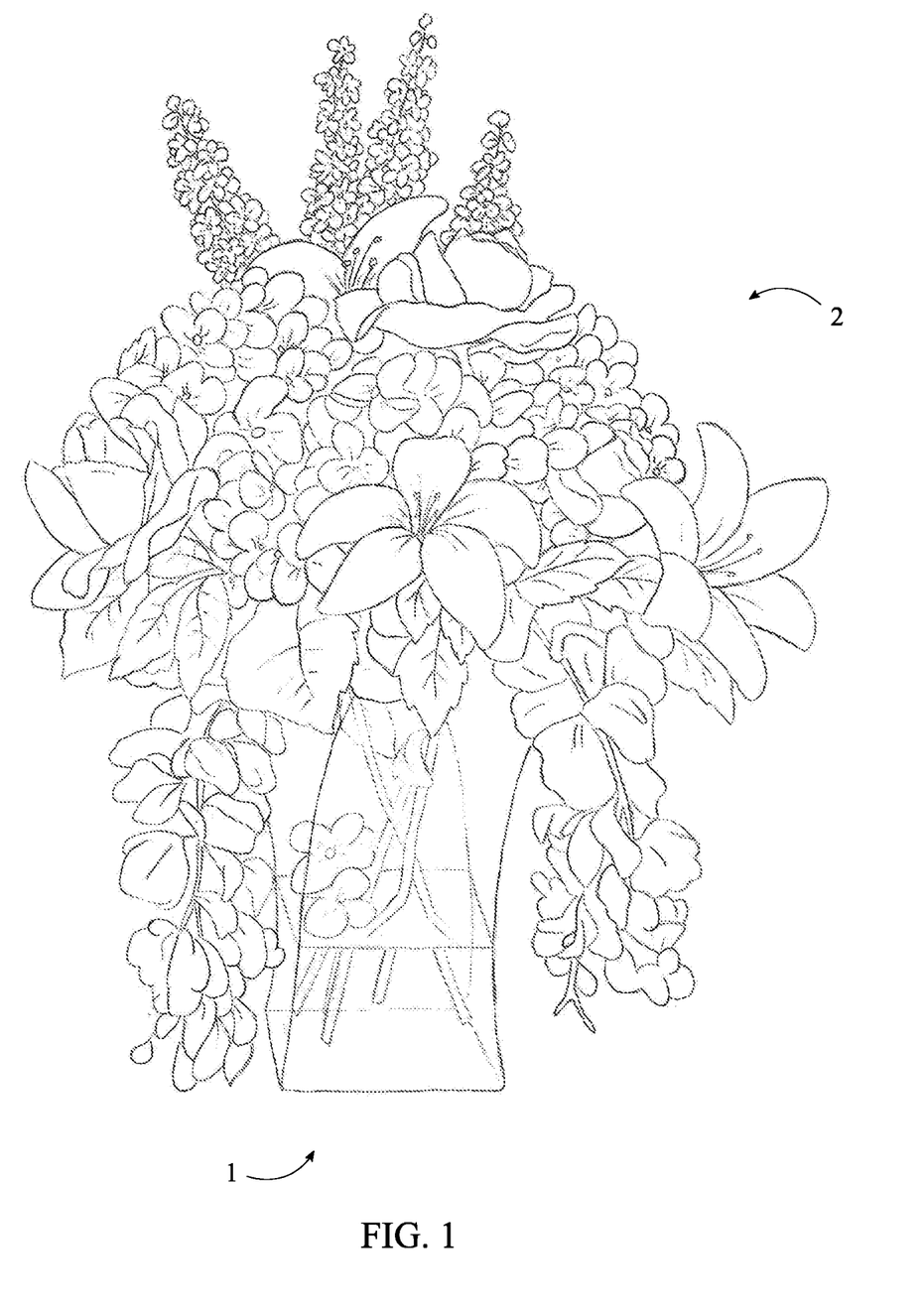
FIG. 1 is a perspective view of the present invention.
Figure 2:
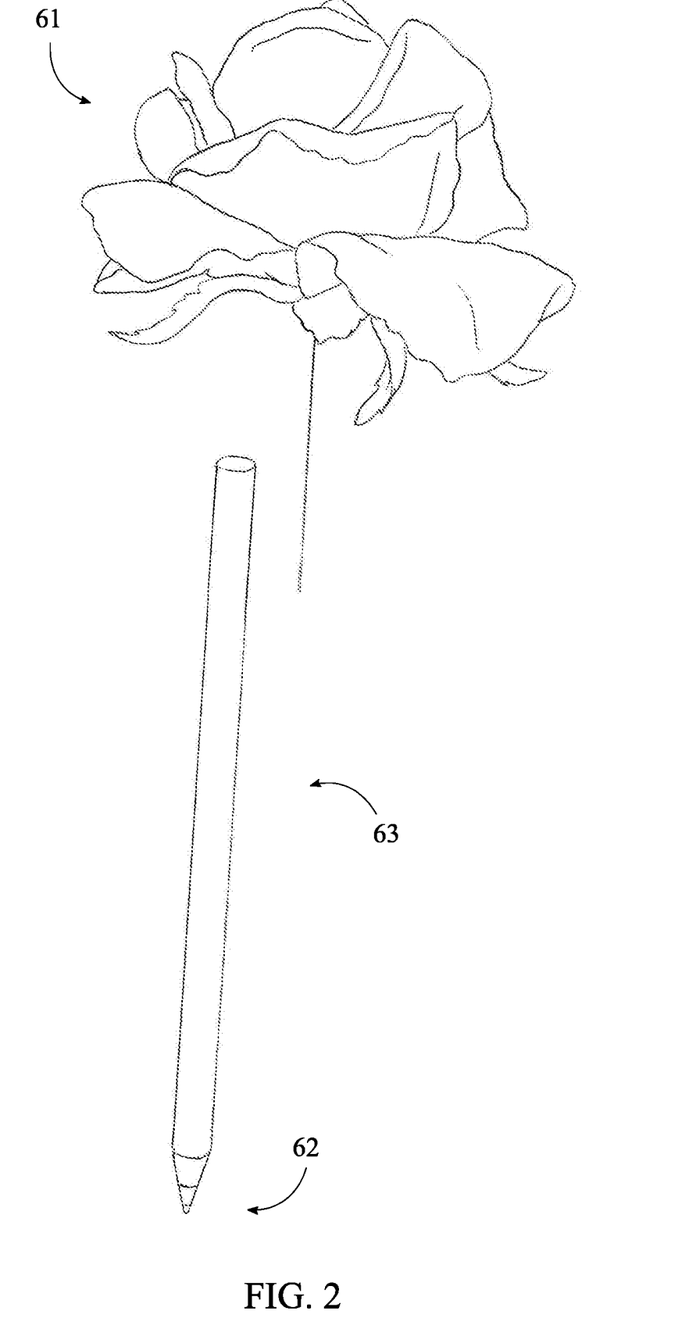
FIG. 2 is an exploded view of a decorative writing utensil according to some embodiments of the present invention.
Figure 3:
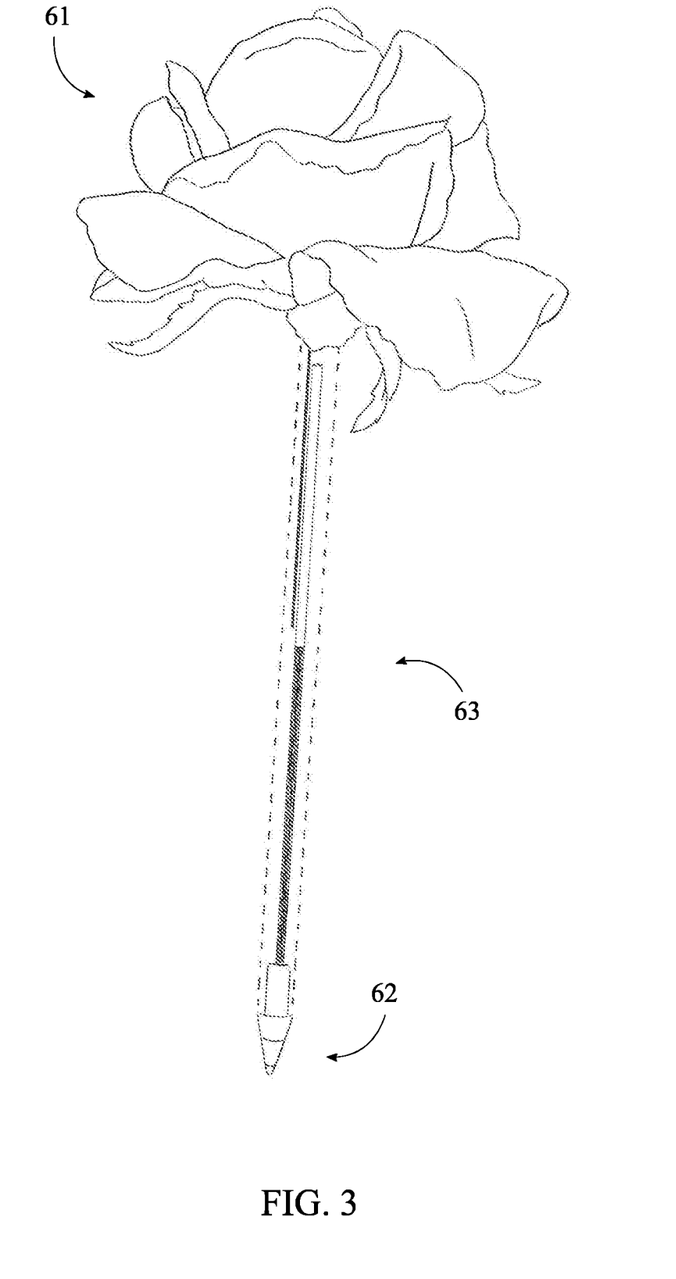
FIG. 3 is an internal view of the decorative writing utensil.

As seen in FIGS. 2-3, in the preferred embodiment of the present invention, each of the plurality of decorative writing utensils 6 comprises an artificial flower 61 head, a writing tip 62, and a body 63. The writing tip 62 is terminally attached to the body 63, and the artificial flower 61 head is terminally attached to the body 63 opposite the writing tip 62. Preferably, the artificial flower 61 head is shaped to resemble a rose, though in various embodiments the artificial flower 61 head may be shaped to resemble any desired flower, plant or other shape. Furthermore, in some embodiments, each of the plurality of decorative writing utensils 6 may be made of or comprise an exterior layer of an absorbent material or a material of a similar quality which may retain the scent of any oils or other scented substances for an extended period of time.

In some embodiments, each of the plurality of decorative writing utensils 6 comprises: a head, a stem, a wire, a pen, and an adhesive. The head is the floral portion of the plurality of blooms that blends in with the bouquet. More specifically, the head resembles a rose, and/or any other type of floral bud that can blend in, but distinguishes from the appearance of the plurality of flowers. The stem is directly attached to the foundation end of the head. More specifically, the stem is a wire that stabilizes and secures the head on to the pen. The pen is inserted and concealed in to the body portion of the bouquet. In some embodiments, the pen may further comprise: a case, a tip, a barrel, and a dye. The case is the chassis of the pen. More specifically, the case is a tubular member that houses the tip and the barrel of the pen. Additionally, the one end of the case attaches to the head. The tip is positioned on the other end of the case, opposite to the head end. More specifically, the tip resembles a ball-point pen tip, while the barrel is directly adjacent to the tip. More specifically, the barrel is the tubular member that serves as the ink receptacle of the pen. In the preferred embodiment of the present invention, the barrel and the tip of the pen is replaceable via refills. The dye coats the case of the pen. More specifically, the dye is a staining member that makes the case appear more realistic. In some embodiments, the adhesive is located between the head end of the case. More specifically, the adhesive permanently fixes the head on to the case.

Figure 11:
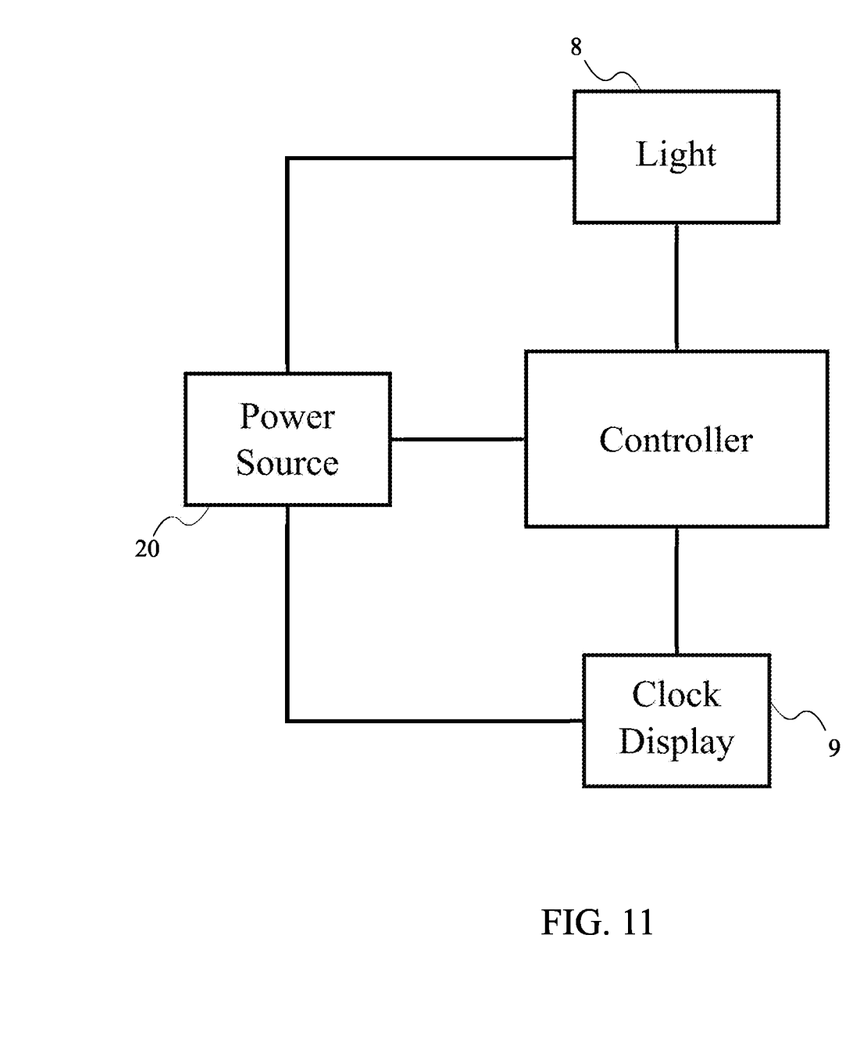
FIG. 11 is a diagram showing electrical connections in one embodiment of the present invention.

Referring to FIG. 11, in some embodiments, the present invention may further comprise a light 8 and a power source 20. The light 8 is positioned within the vase 1 adjacent to the base 11, and the light 8 is electrically connected to the power source 20. The light 8 is an illumination member that resides in the base 11 end of the vase 1 that illuminates the vase 1 and/or artificial floral arrangement 2 in low light settings. In various embodiments of the present invention, the light 8 can be manually actuated via switch and/or automatically actuated via light sensor. In the preferred embodiment of the present invention, the light 8 is battery powered. In other embodiments, the light 8 may be powered by a wired connection to a typical electrical wall socket.

In some embodiments, the present invention may further comprise a clock display 9. The clock display 9 is externally positioned on the vase 1 and electrically connected to the power source 20. In some embodiments, the clock will reside on the base 11 end of the vase 1. More specifically, the clock is any type of digital and/or analog clock that provides the user with the time. In the preferred embodiment of the present invention, the clock is a battery powered clock. In other embodiments, the clock may be powered through a wired connection to a typical electrical wall socket.

Figure 5:
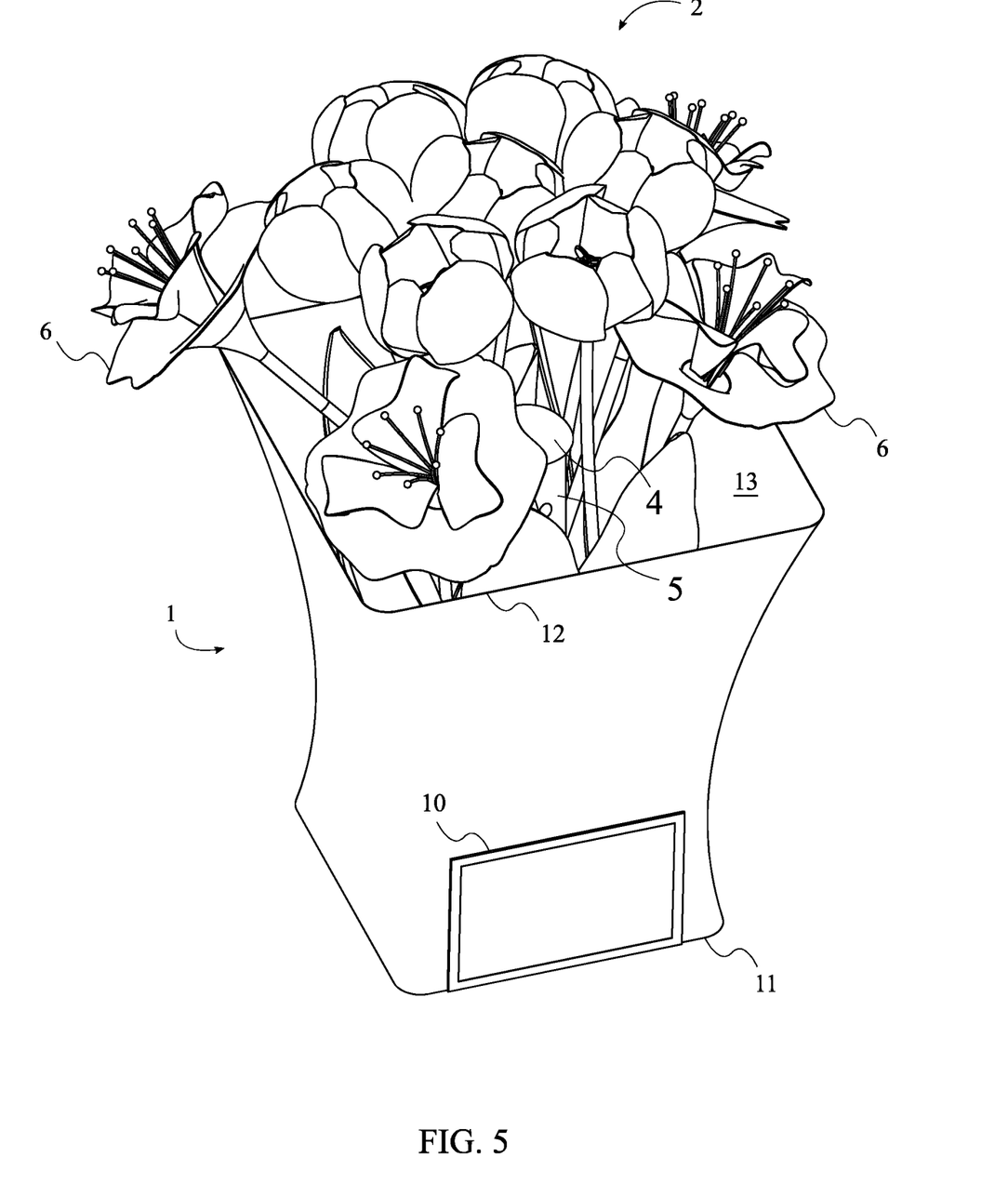
FIG. 5 is a perspective view of one embodiment of the present invention.
Figure 6:
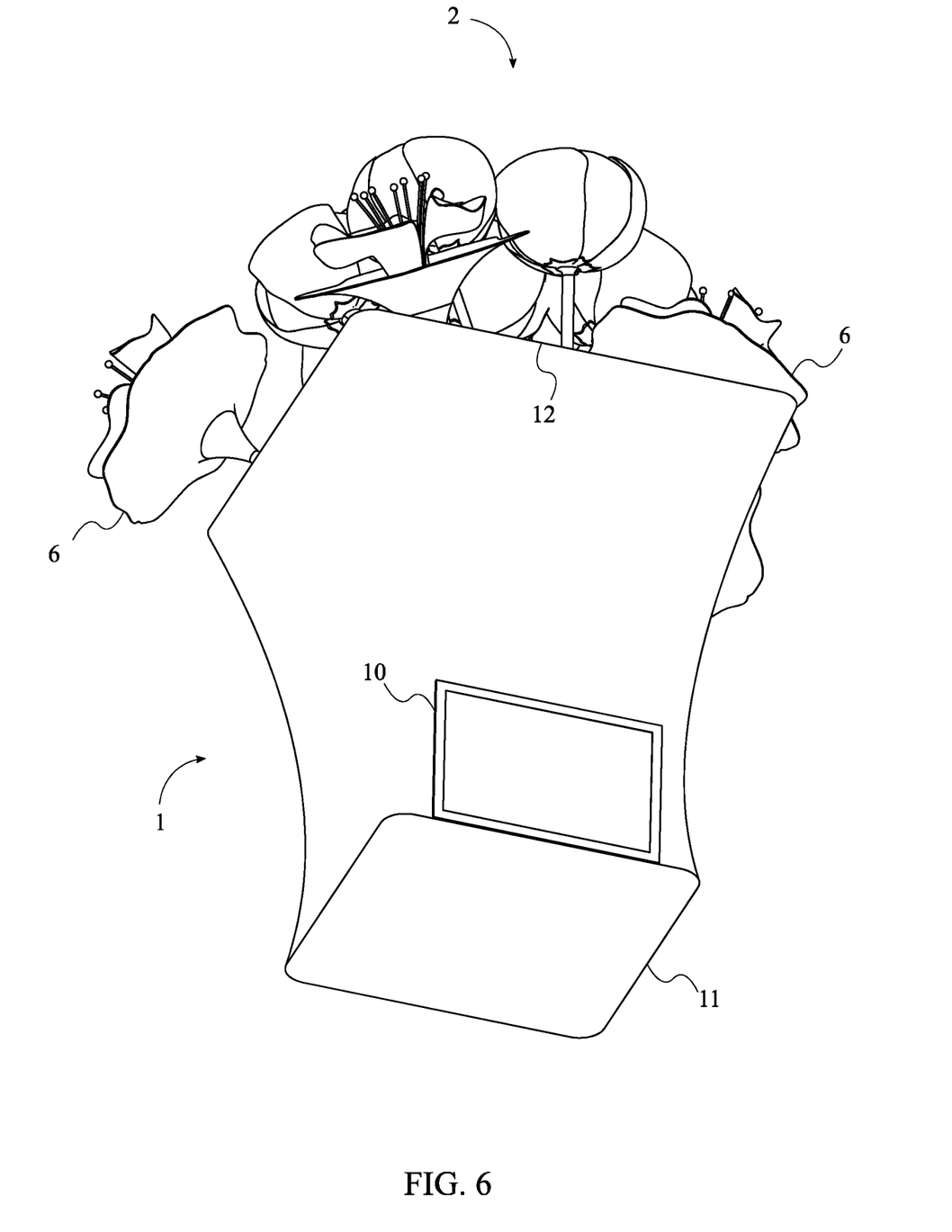
FIG. 6 is a lowered perspective view of one embodiment of the present invention.
Figure 7:
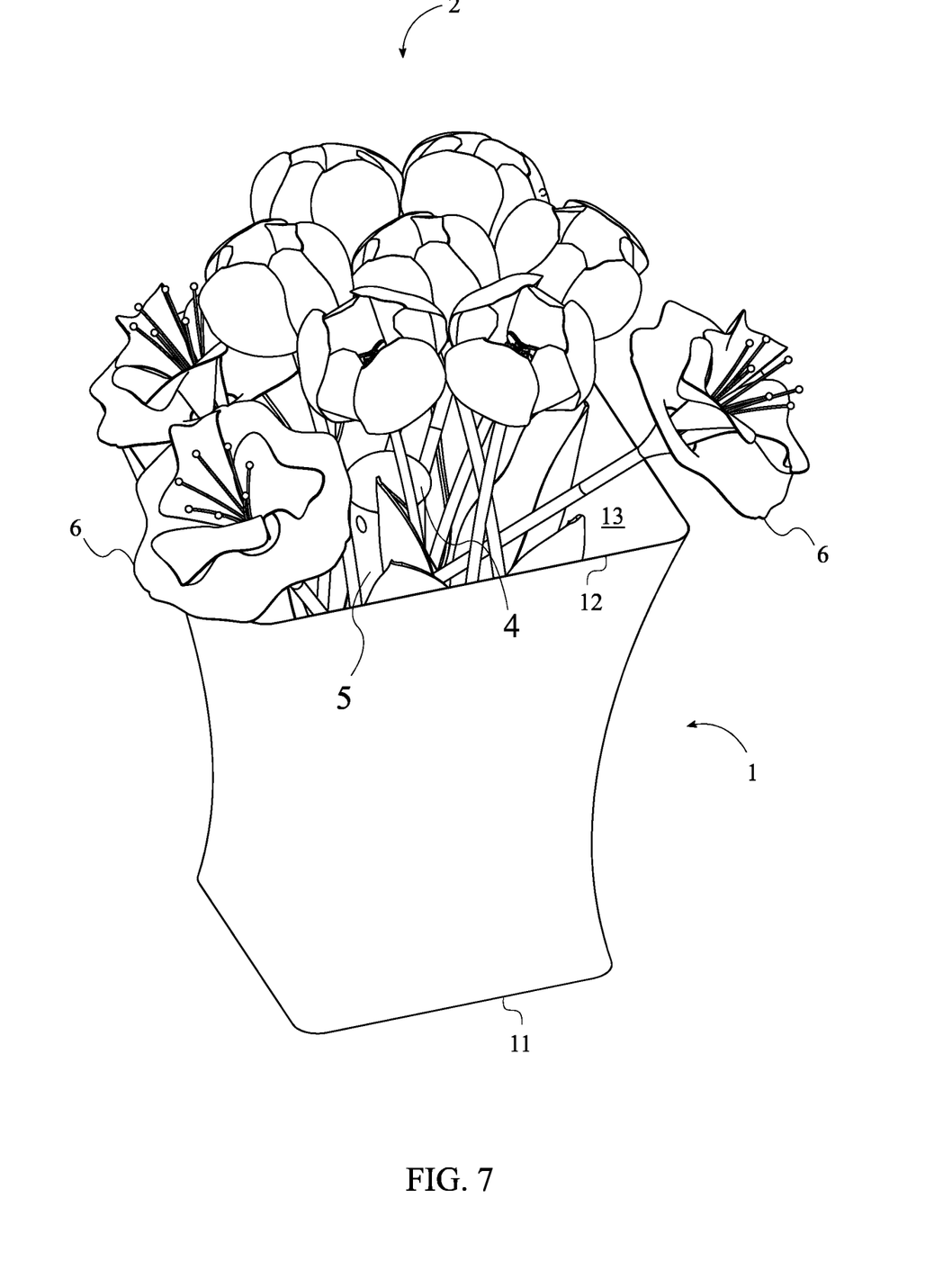
FIG. 7 is a rear perspective view of one embodiment of the present invention.
Figure 8:
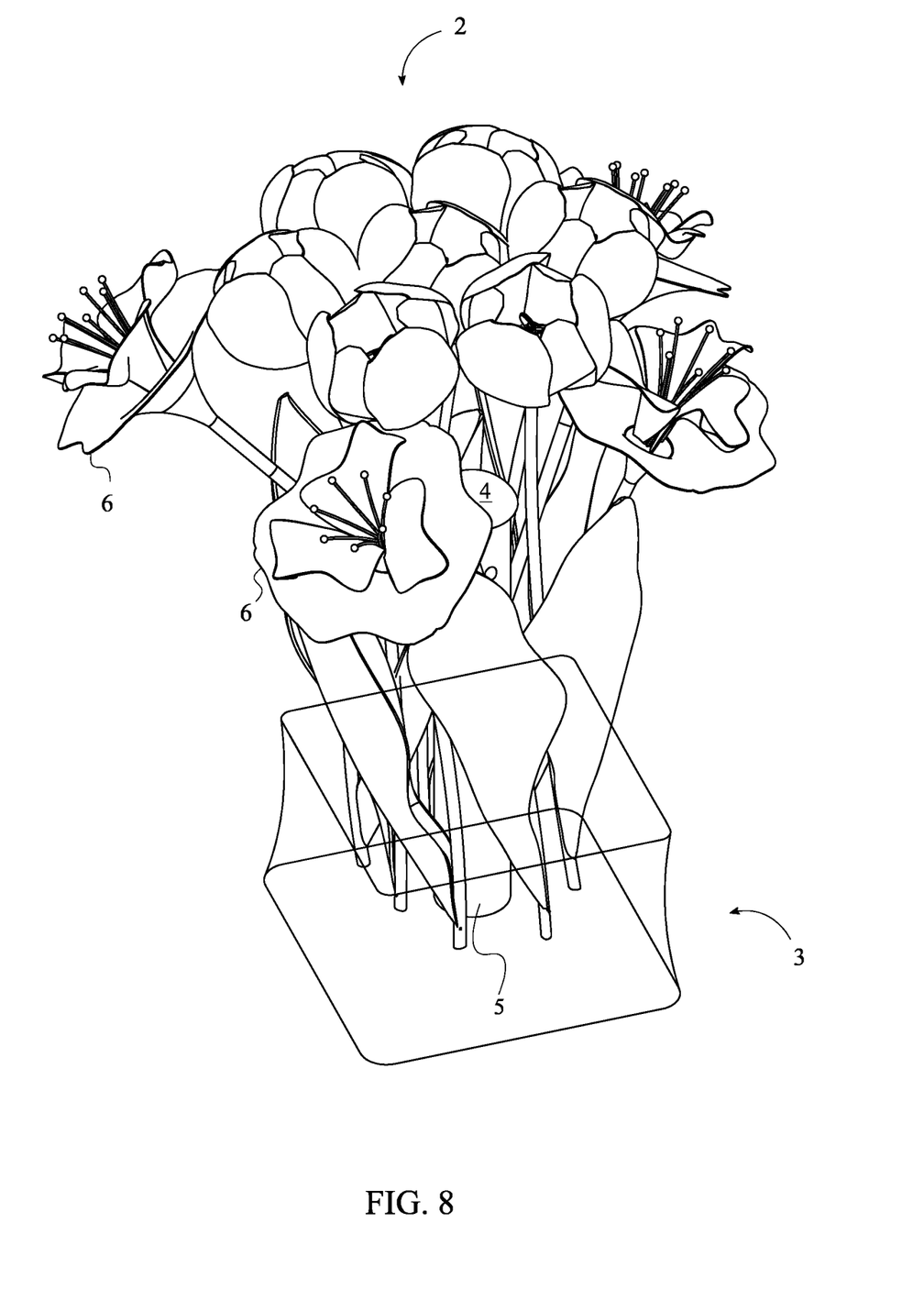
FIG. 8 is a perspective view of one embodiment of the present invention with the vase not shown.

In some embodiments, the present invention may further comprise a card holder 10, as seen in FIGS. 5-6. The card holder 10 is externally connected to the vase 1 adjacent to the base 11. More specifically, the card holder 10 is a receptacle which can receive a label, writeable greeting card, or gift card or similar item in order to provide a visible message, logo, slogan or other visual element on the exterior of the present invention.

Although the invention has been explained in relation to its preferred embodiment, it is to be understood that many other possible modifications and variations can be made without departing from the spirit and scope of the invention as hereinafter claimed.

What is claimed is:

1. A scented flower writing utensil arrangement comprises:
   a vase;
   an artificial floral arrangement;
   a quantity of simulated water medium;
   a scented core;
   a writing utensil holder;
   a plurality of decorative writing utensils;
   the vase comprises a base, a brim, and an opening;
   the base and the brim being positioned opposite each other along the vase;
   the opening being delineated by the brim;
   the quantity of simulated water medium being positioned within the vase adjacent to the base;
   the artificial floral arrangement traversing into the vase through the opening;
   the artificial floral arrangement comprises a plurality of flowers and plurality of stems;
   each of the plurality of flowers being terminally connected to a respective one of the plurality of stems;
   the plurality of stems being connected within the quantity of simulated water medium;
   the artificial floral arrangement being arranged around the scented core and the writing utensil holder;
   the writing utensil holder comprises a body and a plurality of receptacles;
   each of the plurality of writing utensil receptacles traversing into the body of the writing utensil holder; and
   each of the plurality of decorative writing utensils being removably positioned into a respective one of the plurality of receptacles.

2. The scented flower writing utensil arrangement as claimed in claim 1 comprises:
   the quantity of simulated water medium being a self-curing agent.

3. The scented flower writing utensil arrangement as claimed in claim 1 comprises:
   the quantity of simulated water medium being a translucent material.

4. The scented flower writing utensil arrangement as claimed in claim 1 comprises:
   the scented core being a sponge.

5. The scented flower writing utensil arrangement as claimed in claim 1 comprises:
   a quantity of scented oil; and
   the quantity of scented oil being distributed onto the scented core.

6. The scented flower writing utensil arrangement as claimed in claim 1 comprises:
   each of the plurality of decorative writing utensils comprises an artificial flower, a writing tip, and a body;
   the writing tip being terminally attached to the body; and
   the artificial flower being terminally attached to the body opposite the writing tip.

7. The scented flower writing utensil arrangement as claimed in claim 1 comprises:
   a light;
   a power source;
   the light being positioned within the vase adjacent to the base; and
   the light being electrically connected to the power source.

8. The scented flower writing utensil arrangement as claimed in claim 1 comprises:
   a clock display;
   a power source;
   the clock display being externally positioned on the vase; and
   the clock display being electrically connected to the power source.

9. The scented flower writing utensil arrangement as claimed in claim 1 comprises:
   a card holder; and
   the card holder being externally connected to the vase adjacent to the base.

\* \* \* \* \*